United States Patent [19]

Nakashima et al.

[11] Patent Number: 4,492,789
[45] Date of Patent: Jan. 8, 1985

[54] EPOXY RESIN COMPOSITION

[75] Inventors: Kazuhide Nakashima, Ichihara; Takayuki Saito, Hitachi; Takeshi Nakahara, Chiba; Shigeo Tanaka, Ichihara, all of Japan

[73] Assignee: Hitachi Chemical Company, Ltd., Tokyo, Japan

[21] Appl. No.: 481,359

[22] Filed: Apr. 1, 1983

Related U.S. Application Data

[63] Continuation of Ser. No. 392,249, Jun. 25, 1982, abandoned.

[30] Foreign Application Priority Data

Jun. 30, 1981 [JP]    Japan ................................ 56-102964

[51] Int. Cl.$^3$ .............................................. C08G 59/16
[52] U.S. Cl. ..................................... 525/531; 525/533; 525/530; 528/88; 528/92; 528/93; 528/94; 528/112; 528/116; 528/354; 528/355; 528/356

[58] Field of Search ............... 525/530, 531, 533, 507; 528/88, 92, 93, 94, 112, 116, 354, 355, 356

[56] References Cited

U.S. PATENT DOCUMENTS 3,203,920  8/1965  Nikles et al. ........................ 525/533

FOREIGN PATENT DOCUMENTS 1142863  1/1963  Fed. Rep. of Germany .

Primary Examiner—Allan M. Lieberman
Assistant Examiner—Robert E. L. Sellers
Attorney, Agent, or Firm—Antonelli, Terry & Wands

[57] ABSTRACT

An epoxy resin composition comprising (a) an epoxy resin, (b) a lactone obtained by decarboxylation condensation reaction of a saturated alicyclic 1,2-dicarboxylic acid anhydride, and if necessary (c) a curing agent for the epoxy resin and (d) a curing accelerator gives a cured article showing almost no or very slight curing shrinkage.

11 Claims, 1 Drawing Figure

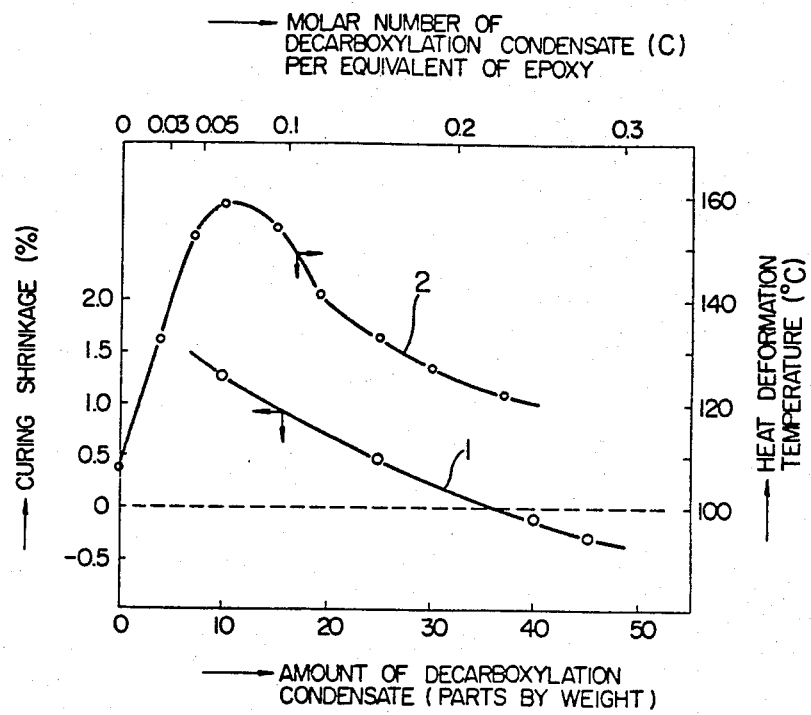

EPOXY RESIN COMPOSITION

This is a continuation of application Ser. No. 392,249, filed June 25, 1982, now abandoned.

This invention relates to an epoxy resin composition comprising an epoxy resin and a lactone which is a decarboxylation condensate of a saturated alicyclic 1,2-dicarboxylic acid anhydride, and is useful as a resin for lamination, a coating material, an adhesive, a casting resin, and the like.

In recent years, epoxy resins have come to play an important role as industrial materials, however they have serious disadvantages in practical use, for example, formation of cracks and concentration of stress against an inserted material which are caused by curing shrinkage.

As a method for preventing these phenomena, there have heretofore generally been employed, for example, the addition of an inorganic filler and a thermoplastic resin and the like or the moderation of curing conditions. However, there has been made almost no substantial improvement, i.e., reduction in curing shrinkage during the curing reaction of an epoxy resin with a curing agent.

This invention solves this problem and provides an epoxy resin composition giving a cured article showing almost no or very slight curing shrinkage by using a novel epoxy-resin-curing agent.

That is to say, this invention relates to an epoxy resin composition comprising:

(a) an epoxy resin, and
(b) a lactone which is a decarboxylation condensate of a saturated alicyclic 1,2-dicarboxylic acid anhydride.

The attached drawing is a graph showing the results (curing shrinkages and heat deformation temperatures) obtained in Examples 3 to 12 and Comparative Example 3.

As the epoxy resin (a) used in this invention, compounds having two or more epoxy groups in the molecule can be used. Preferable examples thereof include, epibis type epoxy resins such as diglycidyl ether of bisphenol A; novolak type epoxy resins such as glycidyl ethers of phenol novolak, cresol novolak and the like; glycidyl ester type epoxy resins such as glycidyl esters of phthalic acid, hexahydrophthalic acid, dimer acid and the like; alicyclic epoxy resins such as 3,4-epoxycyclohexylmethyl-3,4-epoxycyclohexanecarboxylate; glycidyl ethers of polyhydric alcohols such as polypropylene glycol diglycidyl ethers; N-glycidyl compounds of aromatic amines such as diglycidylaniline, diglycidyltoluidine and the like; etc.

The component (b), i.e., the lactone which is a decarboxylation condensate of a saturated alicyclic 1,2-dicarboxylic acid anhydride is represented by the formula:

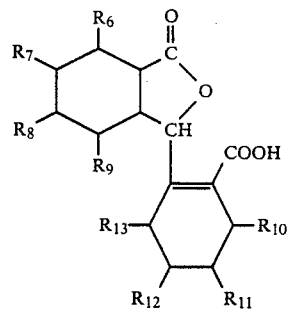

wherein $R_6$, $R_7$, $R_8$, $R_9$, $R_{10}$, $R_{11}$, $R_{12}$ and $R_{13}$ are independently hydrogen or an alkyl group having 1 to 5 carbon atoms. The lactone of the formula (I) can be obtained by allowing a saturated alicyclic 1,2-dicarboxylic acid anhydride to a decarboxylation condensation reaction by heating it in the presence of a basic catalyst.

As the saturated alicyclic 1,2-dicarboxylic acid anhydride, monocyclic saturated alicyclic 1,2-dicarboxylic acid anhydrides are preferred, and there may be exemplified besides them, for example, multi-ring-fused alicyclic 1,2-dicarboxylic acid anhydrides formed by fusion of monocyclic alicyclic structures and containing no unsaturated bond in a ring structure to which an acid anhydride group is attached. Dicarboxylic acids formed by ring-opening of these acid anhydrides may also be used as starting materials, but in this case, they are converted into acid anhydrides once and then give decarboxylation condensates. Further, in this case, the reaction temperature should be raised.

The aforesaid monocyclic saturated alicyclic 1,2-dicarboxylic acid anhydrides include compounds represented by the formula:

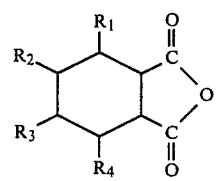

wherein $R_1$, $R_2$, $R_3$ and $R_4$ are independently hydrogen or an alkyl group having 1 to 5 carbon atoms and may be the same or different.

Among these monocyclic saturated alicyclic 1,2-dicarboxylic acid anhydrides, compounds represented by the formula:

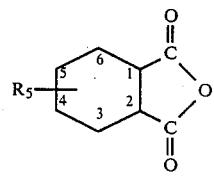

wherein $R_5$ is hydrogen or an alkyl group having 1 to 5 carbon atoms and is attached to the carbon atom at the 3-, 4-, 5- or 6-position in the cyclohexane ring, are more preferred. When $R_5$ is methyl in the formula (III), said compound is particularly preferred as starting material.

The above-mentioned monocyclic saturated alicyclic 1,2-dicarboxylic acid anhydrides include hexahydrophthalic anhydride, 3-methylhexahydrophthalic anhydride, 4-methylhexahydrophthalic anhydride and the like. These may be used alone or as a mixture thereof.

The term "decarboxylation condensate of a saturated alicyclic 1,2-dicarboxylic acid anhydride" means a compound obtained by decarboxylation condensation of 2 molecules of a saturated alicyclic 1,2-dicarboxylic acid anhydride.

The decarboxylation condensation is effected, for example, by heating the aforesaid saturated alicyclic 1,2-dicarboxylic acid anhydride in the presence of a basic catalyst. The basic catalyst includes, for example, amine compounds such as 1,8-diazabicyclo[5,4,0]-undecene-7 (hereinafter abbreviated as "DBU"), 2-ethyl-4-methylimidazole, dibutylaniline, benzyldimethylamine and the like; phosphorus compounds such as triphenylphosphine, hexamethylphosphatriamide and the like; alkali metal hydroxides such as KOH, NaOH and the like; alkali metal alkoxides such as $NaOCH_3$ and the like; hydroxides of alkaline earth metals such as $Mg(OH)_2$, $Ca(OH)_2$, $Ba(OH)_2$ and the like; and oxides of alkaline earth metals such as MgO, CaO, BaO and the like. Among them, DBU, 2-ethyl-4-methylimidazole, KOH, NaOH and the like are preferred.

The amount of these catalysts to be used is preferably 0.1% by weight or more based on the aforesaid saturated alicyclic 1,2-dicarboxylic acid anhydride. When it is less than 0.1% by weight, the reaction becomes slow. The catalyst amount is not particularly limited when it is 0.1% by weight or more but in usual, 5% by weight or less is sufficient.

The reaction temperature is preferably 160° to 250° C. When it is lower than 160° C., the reaction becomes slow. On the other hand, when it is too high, the product is seriously colored and by-products having high molecular weights tend to be formed: therefore it is preferable not exceeding 250° C.

Organic solvents may be used or may not be used.

A condensation product obtained by such a production process is a bimolecular condensation product and has in the molecule one lactone ring, one carboxyl group and at least one double bond (double bond newly introduced into the carbon ring), which can be identified from the NMR spectrum, IR spectrum and a qulitative reaction with $KMnO_4$ of said product. These facts together with the starting material used, elementary analysis results, and the like indicate that the above-mentioned condensation product has two carbon rings, with one of which is fused a lactone ring and to the other of which is attached the aforesaid carboxyl group, and that the aforesaid double bond is present in the latter carbon ring. Carbon atoms in the lactone ring are attached to carbon atoms in the latter carbon ring. For example, when hexahydrophthalic anhydride is used, the following compound is produced as a bimolecular condensation product.

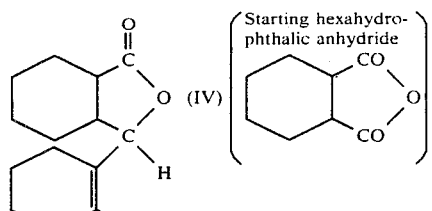

(molecular formula: $C_{15}H_{20}O_4$)

From the compound of the above formula (II), there is generally obtained a lactone, a decarboxylation condensate represented by the formula:

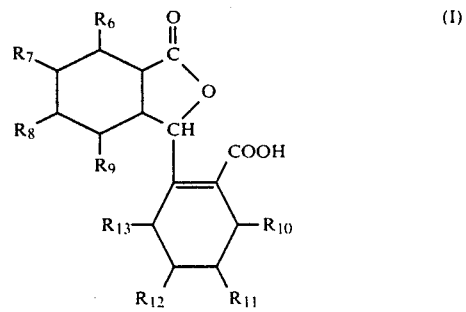

wherein $R_6$, $R_7$, $R_8$, $R_9$, $R_{10}$, $R_{11}$, $R_{12}$ and $R_{13}$ are as defined above.

From a compound represented by the above formula (III), there is obtained a decarboxylation condensate represented by the formula:

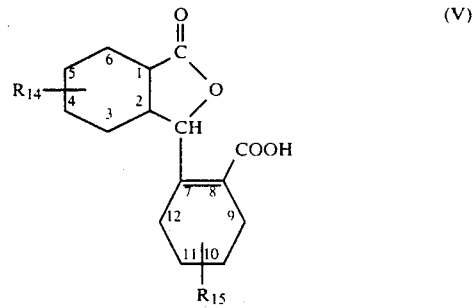

wherein $R_{14}$ and $R_{15}$ are independently hydrogen or an alkyl group having 1 to 5 carbon atoms; the numbers 1 to 12 indicate numbering of the carbon atoms in the cyclohexane ring and the cyclohexene ring; and $R_{14}$ and $R_{15}$ are attached to the carbon atom at the 3-, 4-, 5- or 6-position and the carbon at the 9-, 10-, 11- or 12-position, respectively.

When $R_{14}$ and/or $R_{15}$ are independently a methyl group in the formula (V), the decarboxylation condensate is often a mixture of structural isomers because of the variation in positions of the methyl groups.

The epoxy resin composition of this invention may contain, as a component (c), an acid anhydride known as a curing agent for an epoxy resin such as phthalic anhydride, hexahydrophthalic anhydride, tetrahydrophthalic anhydride, 3,6-endomethylene-tetrahydrophthalic anhydride, methylhexahydrophthalic anhydride, methyltetrahydrophthalic anhydride, metyl-3,6-endomethylene-tetrahydrophthalic anhydride, dodecenylsuccinic anhydride, trimellitic anhydride, pyromellitic anhydride, or the like.

Further, the epoxy resin composition of this invention may further contain as a component (d) a compound known as a curing accelerator, for example, a tertiary amine or a salt thereof, a quaternary ammonium compound, an alkali metal alcoholate, a metal salt of a fatty acid, or the like. Examples of these compounds are benzyldimethylamine, 2,4,6-tris(dimethylaminomethyl)-phenol, 2-ethyl-4-methylimidazole, triamylammonium phenolate, sodium hexanetriol, 1,8-diazabicyclo[5,4,0]-undecene-7, tin stearate, zinc octoate, and the like.

The aforesaid component (b) is preferably used in an amount of 0.01 to 1 mole, particularly 0.03 to 0.5 mole per equivalent amount of the epoxy groups of the component (a). When the amount of the component (b) is too small, the effect of this invention, i.e., an effect of reducing shrinkage during curing is insufficient. When it is too large, the component (b) is present in excess as a curing agent, so that the resulting cured article possesses deteriorated characteristics. The aforesaid component (c) is used in an amount of 0 to 1.5 moles, preferably 0 to 1 mole per equivalent of the epoxy groups of the component (a). When the amount of the component (c) is too large, the curing agents are present in excess, so that the resulting cured article possesses deteriorated characteristics. The components (b) and (c) are used in amounts properly selected so that the sum of amounts of the components (b) and (c) may range from 0.01 to 1.51 moles, preferably from 0.03 to 1.2 moles per equivalent of the epoxy groups of the component (a), and that they may be present neither in excess nor in too small amounts as curing agents and cause no marked deterioration of the curing characteristics.

Further, it is preferable that the aforesaid component (d) is allowed to be present in the epoxy resin composition of this invention during the curing reaction. This is because the curing reaction is relatively slow when there are used the aforesaid component (b) or components (b) and (c) which are curing agents. The amount of the component (d) is 10 parts by weight or less, preferably 0.01 to 10 parts by weight, particularly preferably 0.1 to 5 parts by weight per equivalent of the epoxy groups of the component (a). When the accelerator is too much, a condensation reaction (etherification) of the epoxy resin molecules with one another tends to take place. Therefore, it is not desirable.

The curable composition of this invention may further be mixed with one or more diluents, extenders, inorganic fillers, pigments, dyes, organic solvents, plasticizers, flow-controlling agents, thixotropy-imparting agents, defoaming agents, flame retardants and the like at any step before curing.

Next, production examples of the decarboxylation condensates and examples of this invention are shown below.

PRODUCTION EXAMPLE 1

In a four-necked flask equipped with a stirrer was placed 100 g of hexahydrophthalic anhydride and heated to be melted, after which 1 g of 1,8-diazabicyclo-[5,4,0]undecene-7 (DBU) was added, and a decarboxylation reaction of the hexahydrophthalic anhydride was conducted at 200° C. for 5 hours to obtain a decarboxylation condensate (A) which was a light-yellow solid at ordinary temperatures. This condensate was identified as a compound of the above formula (IV) by its NMR spectrum, IR spectrum, qualitative reaction with KMnO$_4$, elementary analysis, and the like.

PRODUCTION EXAMPLE 2

The same procedure as described in Production Example 1 was followed, with exception that 4-methylhexahydrophthalic anhydride was substituted for the hexahydrophthalic anhydride, to obtain a decarboxylation condensate (B) which was a light-yellow solid at ordinary temperatures.

The decarboxylation condensate (B) was identified, by its NMR spectrum, IR spectrum, qualitative reaction with KMnO$_4$, elementary analysis and the like, as a compound represented by the formula;

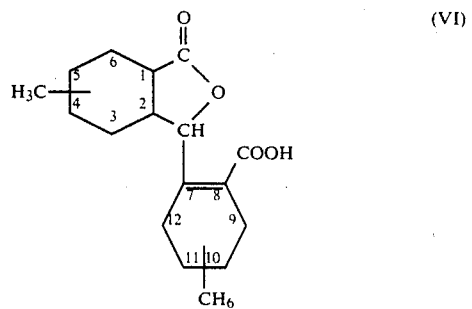

(VI)

wherein the numerals 1 to 12 indicate numbering of the carbon atoms in the cyclohexane ring and the cyclohexene ring, and the two methyl groups are attached to the 4- or 5-position and to the 10- or 11-position, respectively. The compound represented by the formula (VI) may be a mixture of 4 structural isomers, but these isomers are substantially inseparable from one another, and hence said compound is regarded as a unitary compound.

PRODUCTION EXAMPLE 3

A decarboxylation condensate (c) was produced in the same manner as in Production Example 1, except that a mixture consisting of 60% by weight of 3-methylhexahydrophthalic anhydride and 40% by weight of 4-methylhexahydrophthalic anhydride was substituted for the hexahydrophthalic anhydride used in Production Example 1. The decarboxylation condensate (c) was a compound represented by the formula:

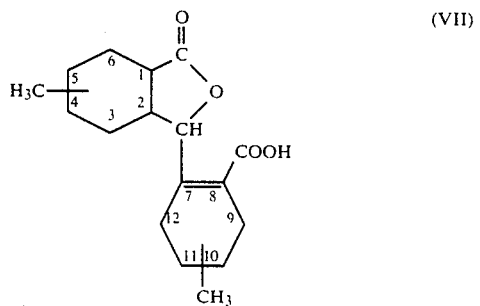

(VII)

wherein the numbers 1 to 12 indicate numbering of the carbon atoms in the cyclohexane ring and the cyclohexene ring, and the two methyl groups are attached to the 3-, 4-, 5- or 6-position and to the 9-, 10-, 11- or 12-position, respectively. As to this compound, there is theoretically considered to produce 16 structural isomers because of variation in the positions to which the two methyl groups are individually attached, and the compound exists as a mixture of these isomers. However, these isomers are substantially individually inseparable from the mixture, and hence the compound is regarded as a unitary compound.

EXAMPLE 1

With 185 parts by weight of an epibis type epoxy resin (GY-250, a trade name, manufactured by Ciba-Geigy Corp., epoxy equivalent: 185) were sufficiently mixed 56 parts by weight (0.21 mole per equivalent of the epoxy groups) of the decarboxylation condensate (A), 112 parts by weight (0.67 mole per equivalent of the epoxy groups) of methyltetrahydrophthalic anhydride (HN-2200, a trade name, manufactured by Hitachi Chemical Co., Ltd.) and 0.93 part by weight of benzyldimethylamine. The resulting composition was heated at 120° C. for 5 hours and then at 150° C. for 15 hours to be cured. The heat deformation temperature of the cured article was 118° C., and its curing shrinkage was found to be 1.9% from the measurement of the true specific gravity at 25° C. before and after the curing.

EXAMPLE 2

With 185 parts by weight of an epibis type epoxy resin (GY-250) were sufficiently mixed 56 parts by weight (0.19 mole per equivalent of the epoxy groups) of the decarboxylation condensate (B), 130 parts by weight (0.77 mole per equivalent of the epoxy groups) of methylhexanhydrophthalic anhydride (NH-5500, a trade name, manufactured by Hitachi Chemical Co., Ltd.) and 1.9 parts by weight of benzyldimethylamine. The resulting cmposition was heated at 130° C. for 50 minutes and then at 125° C. for 7 hours to be cured. The heat deformation temperature of the cured article was 120° C., and its curing shrinage was found to be 1.7% from the measurement of the true specific gravity at 25° C. before and after the curing.

COMPARATIVE EXAMPLES 1 AND 2

Cured articles were obtained by employing formulations and curing conditions shown in Table 1. The characteristics of the cured articles are shown in Table 1.

TABLE 1

|  | Comparative Example 1 | Comparative Example 2 |
|---|---|---|
| GY-250 | 185 parts by weight | 185 parts by weight |
| HN-2200 | 166 | — |
| HN-5500 | — | 185 |
| Benzyldimethylamine | 0.93 | 1.9 |
| Curing conditions | 120° C./5 hr + 150° C./15 hr | 130° C./50 min + 125° C./7 hr |
| Heat deformation temperature | 120° C. | 128° C. |
| Curing shrinkage | 2.6% | 2.4% |

EXAMPLES 3 TO 12 AND COMPARATIVE EXAMPLE 3

With 100 parts by weight of an epoxy resin (GY-250) were sufficiently mixed the decarboxylation condensate (C) in each amount shown in Table 2, and 1 part by weight of imidazole. The thus obtained compositions were heated at 120° C. for 5 hours and then at 150° C. for 15 hours to be cured, whereby cured articles were obtained. The results of measurement of the heat deformation temperatures and curing shrinkages of the cured articles are shown in Table 2.

TABLE 2

|  | Comparative Example 3 | Examples |  |  |  |  |  |  |  |  |  |
|---|---|---|---|---|---|---|---|---|---|---|---|
|  |  | 3 | 4 | 5 | 6 | 7 | 8 | 9 | 10 | 11 | 12 |
| Amount of decarboxylation condensate (C) [parts by weight] *1 | 0 (0) | 4 (0.025) | 7 (0.044) | 10 (0.063) | 15 (0.092) | 19 (0.116) | 25 (0.154) | 30 (0.185) | 37 (0.228) | 40 (0.246) | 45 (0.277) |
| Heat deformation temperature (°C.) | 107 | 132 | 152 | 159 | 154 | 141 | 133 | 127 | 121 | — | — |
| Curing shrinkage *2 (%) | — | — | 1.3 | — | — | — | 0.5 | — | — | −0.2 | −0.3 |

Note
*1 Numerical values in parentheses indicate the number of moles of the decarboxylation condensate (C) per equivalent of the epoxy groups of the epoxy resin.
*2 The curing shrinkage values with a minus sign indicate that the cured articles were expanded.

An illustration of the results is shown as FIG. 2.

In above Examples 1 to 12 and Comparative Examples 1 to 3, each curing shrinakge was obtained by mixing the epoxy resin and each decarboxylation condensate and/or acid anhydride, heating the resulting mixture to 120° C. to be made into a homogeneous solution, cooling the solution to 25° C., measuring the true specific gravity "a" of the solution, thereafter adding each curing accelerator, obtaining a cured article under the curing conditions described in each of Examples and Comparative Examples, measuring the true specific gravity "b" of the cured article at 25° C., and then calculating the curing shrinkage from the formula:

$$(b-a)/a \times 100\%.$$

The epoxy resin composition of this invention gives a cured article having only a slight curing shrinkage. Therefore, the formation of cracks in the cured article can be reduced, and the cured article is excellent in dimensional stability. Particularly when used as a casting resin, said epoxy resin composition brings about the above-mentioned effect most sufficiently. When an electronic part or the like is encapsulated with said composition, stress on an element or a semiconductor can be reduced, and the reliability can be improved.

What is claimed is:

1. An epoxy resin composition comprising
   (a) an epoxy resin, and
   (b) a lactone represented by the formula:

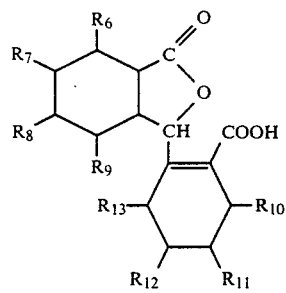

wherein the group represented by $R_6$, $R_7$, $R_8$, $R_9$, $R_{10}$, $R_{11}$, $R_{12}$ and $R_{13}$ are independently hydrogen or an alkyl group having 1 to 5 carbon atoms, at least one of said group being an alkyl group.

2. An epoxy resin composition according to claim 1, which further comprises (c) a curing agent for the epoxy resin.

3. An epoxy resin composition according to claim 1, which further comprises:

(c) a curing agent for the epoxy resin, and (d) a curing accelerator.

4. An epoxy resin composition according to claim 1, 2 or 3, wherein the lactone (b) is represented by the formula:

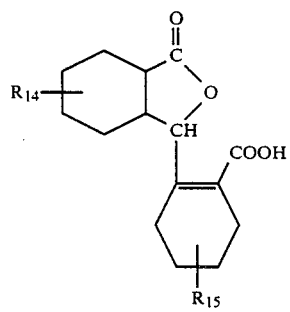

wherein $R_{14}$ and $R_{15}$ are independently an alkyl group having 1 to 5 carbon atoms.

5. An epoxy resin composition according to claim 1, 2 or 3 wherein the lactone (b) is

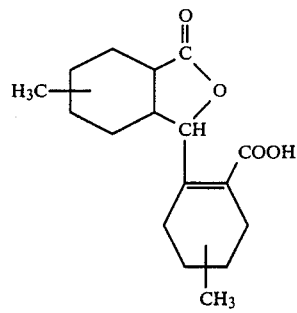

6. An epoxy resin composition according to claim 1, 2 or 3, wherein the lactone (b) is

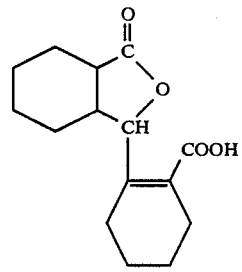

7. An epoxy resin composition accoding to claim 1, wherein the lactone (b) is used in an amount of 0.01 to 1 mole per equivalent amount of the epoxy group in the epoxy resin (a).

8. An epoxy resin composition according to claim 2, wherein the lactone (b) is used in an amount of 0.01 to 1 mole, the curing agent (c) is used in an amount of upto 1.5 moles, and the total of the compounds (b) and (c) is 0.01 to 1.51 moles per equivalent amount of the epoxy group in the epoxy resin (a).

9. An epoxy resin composition according to claim 3, wherein the components (b) and (c) are used in a total amount of 0.01 to 1.51 moles and the component (d) is used in an amount of 0.01 to 10 party by weight, per equivalent amount of the epoxy group in the epoxy resin (a).

10. A composition according to claim 2 or 3, wherein the curing agent (c) is phthalic anhydride, hexahydrophthalic anhydride, tetrahydrophthalic anhydride, 3,6-endomethylene-tetrahydrophthalic anhydride, methylhexahydrophthalic anhydride, methyltetrahydrophthalic anhydride, methyl-3,6-endomethylenetetrahydrophthalic anhydride, dodecenylsuccinic anhydride, trimellitic anhydride, or pyromellitic anhydride.

11. A composition according to claim 3, wherein the curing accelerator (d) is a tertiary amine, a salt of tertiary amine, a quaternary ammonium compound, an alkali metal alcoholate, or a metal salt of a fatty acid.

* * * * *